United States Patent [19]

Takematsu et al.

[11] Patent Number: 5,169,425
[45] Date of Patent: Dec. 8, 1992

[54] HERBICIDAL COMPOSITIONS COMPRISING 2-AMINO-4-ARYLALKYLAMINO-6-HALOALKYL-1,3,5-TRIAZINES AND CHLOROPHENOXY ACIDS AND, OPTIONALLY, SUBSTITUTED UREAS

[75] Inventors: Tetsuo Takematsu, Utsunomiya; Toshihiro Hirata, Sodegaura; Izumi Kobayashi, Tokyo; Nobuyuki Kikkawa, Sodegaura, all of Japan

[73] Assignee: Idemitsu Kosan Company Limited, Tokyo, Japan

[21] Appl. No.: 716,534

[22] Filed: Jun. 17, 1991

[30] Foreign Application Priority Data

Jun. 29, 1990 [JP] Japan .................. 2-169761
Apr. 10, 1991 [JP] Japan .................. 3-103511

[51] Int. Cl.$^5$ ............... A01N 43/08; A01N 43/10; A01N 43/68; A01N 47/30
[52] U.S. Cl. ............................. 71/88; 71/90; 71/93; 71/120
[58] Field of Search ............ 71/110, 93, 88, 90

[56] References Cited

U.S. PATENT DOCUMENTS 4,844,731 7/1989 Takematsu et al. ................ 71/93
4,932,998 6/1990 Takematsu et al. ................ 71/90

FOREIGN PATENT DOCUMENTS 63-51379 3/1988 Japan .
WO90/09378 8/1990 World Int. Prop. O. .

OTHER PUBLICATIONS

The *Agrachemicals Handbook*, "2,4-D" 1987.

*Primary Examiner*—Richard L. Raymond
*Assistant Examiner*—S. Mark Clardy
*Attorney, Agent, or Firm*—Frishauf, Holtz, Goodman & Woodward

[57] ABSTRACT

Herbicidal compositions comprising as active ingredients a triazine derivative represented by general formula [I]:

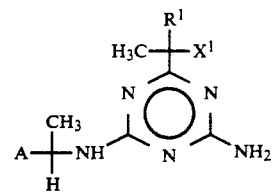

and phenoxy type herbicides represented by general formula [II]:

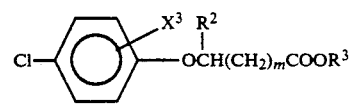

and herbicidal compositions comprising as active ingredients a triazine derivative represented by general formula [I]:

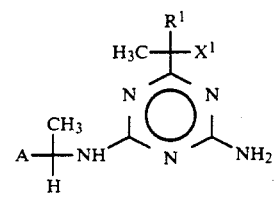

phenoxy type herbicides represented by general formula [II]:

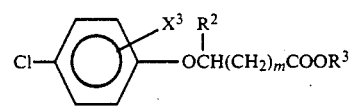

and urea type herbicides represented by general formula [III]:

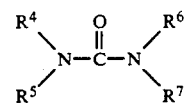

By synergistic effects of the active ingredients, the herbicidal compositions show a high herbicidal effect at low dosage and have such a wide range of herbicidal spectrum that the compositions exhibit their high herbicidal effect not only against broad-leaved weeds but also against Gramineae weeds, etc. The compositions have flexibility of treatment to exhibit effectiveness as compared to known herbicides for field crops and are free from injury.

14 Claims, No Drawings

HERBICIDAL COMPOSITIONS COMPRISING 2-AMINO-4-ARYLALKYLAMINO-6-HALOALKYL-1,3,5-TRIAZINES AND CHLOROPHENOXY ACIDS AND, OPTIONALLY, SUBSTITUTED UREAS

BACKGROUND OF THE INVENTION

1. Field of the Invention

The present invention relates to herbicidal compositions comprising triazine derivatives and phenoxy type herbicides as active ingredients, and herbicidal compositions comprising triazine derivatives, phenoxy type herbicides and urea type herbicides as active ingredients.

2. Statement of the Prior Art

Heretofore a variety of herbicides have been developed and have contributed to agricultural productivity and saving labors. However, some herbicides have been used over many years and hence, weeds which are insufficiently controlled are increasing. It has thus been desired to develop herbicides having a wide range of herbicidal spectrum and those effective also against such troublesome weeds. Also in order to remove environmental pollution problems caused by conventional berbicides, it has been desired to develop berbicides having a high activity at a low dosage. Moreover, in order to control weeds emerging non-uniformly over a long period of time, it has been desired to develop herbicides having an excellent residual activities and having flexibility of treatment to exhibit effectiveness even though the treatment is performed over a long period from pre-emergence to a wide range of growing stage of weeds.

Under such a situation, the present inventors found that specific, novel triazine derivatives containing a halo alkyl are compounds which show a high herbicidal effect against troublesome weeds both by soil treatment and by foliage treatment, without causing any phytotoxicities of Gramineae field crops, and moreover provide an excellent effectiveness against weeds in paddy fields (Japanese Patent Application Nos. 1-38178 and 1-154465). The present inventors made extensive investigations to further improve the herbicidal activity of the triazine derivatives.

As a result, it has been found that compositions comprising the triazine derivatives in combination with specific phenoxy type herbicides exhibit an excellent herbicidal activity which is unexpected from each of the herbicides, show their herbicidal effect at low dosage and have a wide range of herbicidal spectrum especially against broad-leaved weeds. It has also been found that compositions comprising the triazine derivative in combination with specific phenoxy type herbicides and specific urea type herbicides have a wide range of herbicidal spectrum against weeds including Gramineae weeds. The present invention has thus been accomplished.

SUMMARY OF THE INVENTION

That is, the present invention provides firstly herbicidal compositions comprising as active ingredients triazine derivatives represented by general formula [I]:

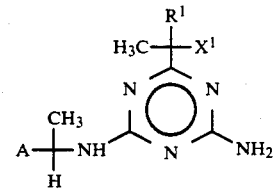

(wherein A represents the following formula (a):

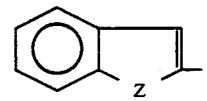

(wherein Z represents oxygen atom or sulfur atom), or formula (b):

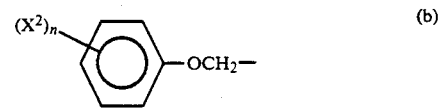

(wherein $X^2$ represents methyl group or fluorine atom and n represents 0 or an integer of 1 or 2); $R^1$ represents hydrogen atom or methyl group; and $X^1$ represents fluorine atom or chlorine atom) and phenoxy type herbicides represented by general formula [II]:

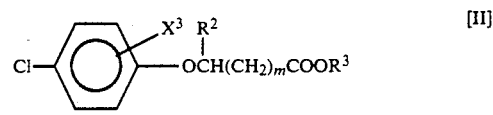

(wherein $X^3$ represents methyl group or chlorine atom; $R^2$ represents hydrogen atom or methyl group; $R^3$ represents hydrogen atom, an alkyl group having 1 to 4 carbon atoms, an alkenyl group having 1 to 4 carbon atoms, sodium atom or $NH_4$; and m represents 0 or an integer of 1 to 3); and secondly herbicidal compositions comprising as active ingredients triazine derivatives represented by general formula [I]:

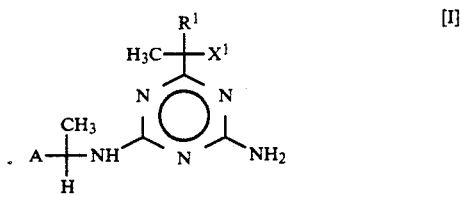

(wherein A, $R^1$ and $X^1$ have the same significances as described above), phenoxy type herbicides represented by general formula [II]:

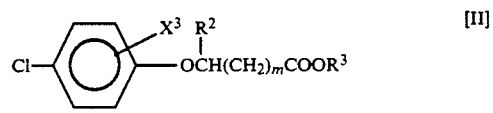

(wherein $R^2$, $R^3$ and $X^3$ have the same significances as described above), and urea type herbicides represented by general formula [III]:

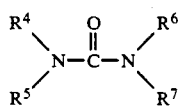

(wherein R⁴ represented a benzene ring or an aromatic hetero ring, which may be optionally substituted; R⁵ represents hydrogen atom or a straight or branched alkyl group having 1 to 6 carbon atoms; R⁶ represents a straight or branched alkyl group having 1 to 6 carbon atoms; and R⁷ represents hydrogen atom or a straight or branched alkyl group or a branched alkoxy group, having 1 to 6 carbon atoms).

DETAILED DESCRIPTION OF THE INVENTION

The first herbioidal composition of the present invention comprises as active ingredients the triazine derivatives represented by general formula [I] described above and the phenoxy type herbicides represented by general formula [II] described above.

Specific examples of the triazine derivatives represented by general formula [I] described above include:
2-amino-4-[1-(benzofuran-2'-yl)ethylamino]-6-(α-fluoro,α-methylethyl)-s-triazine

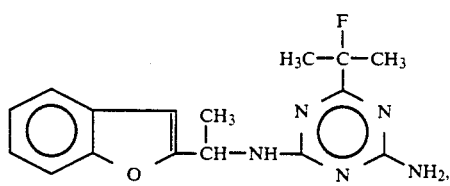

2-amino-4-[1-(benzofuran-2'-yl)ethylamino]-6-(α-fluoroethyl)-s-triazine

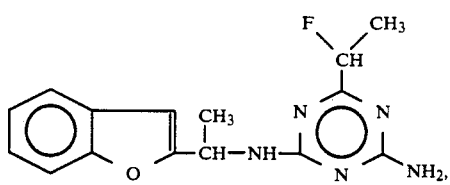

2-amino-4-[1-(benzothiophen-2'-yl)ethylamino]-6-(α-fluoro,α-methylethyl)-s-triazine

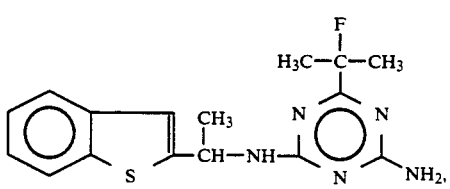

2-amino-4-(α-fluoro,α-methylethyl)-6-[2-(3',5'-dimethylphenoxy)-1-methylethylamino]-s-triazine

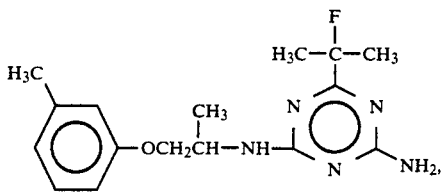

2-amino-4-(α-fluoro,α-methylethyl)-6-[2-(3'fluorophenoxy)-1-methylethylamino]-s-triazine

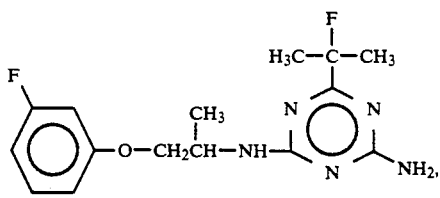

2-amino-4-(α-chloro,α-methylethyl)-6-[2-(3',5'-dimethylphenoxy)-1-methylethylamino]-s-triazine

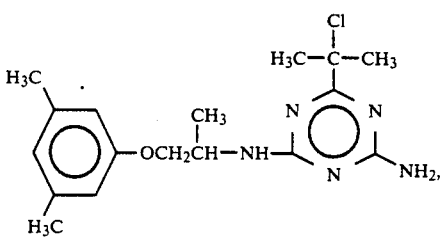

2-amino-4-(α-fluoro,α-methylethyl)-6-[2-(3',5'-dimethylphenoxy)-1-methylethylamino]-s-triazine

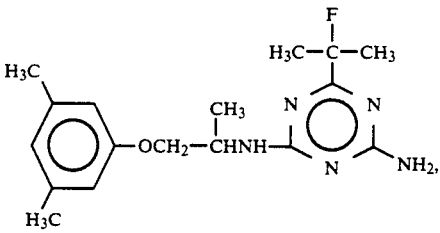

etc.

The triazine derivatives represented by general formula [I] described above may be prepared by various processes. Among these processes, an advantageous process comprises reacting alkyl amine salts represented by general formula [IV]:

(wherein A has the same significance as described above and X⁴ represents a halogen atom) with cyanoguanidine represented by the following formula [c]:

to prepare alkyl biguanide salts represented by general formula [V]:

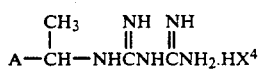

$$A-CH-NHCNHCNH_2 \cdot HX^4 \quad [V]$$

(wherein A and $X^4$ have the same significance as described above); and then reacting the alkyl biguanide salts with alkyl esters represented by general formula [VI]:

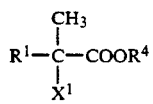

$$R^1-\underset{X^1}{\overset{CH_3}{\underset{|}{C}}}-COOR^4 \quad [VI]$$

(wherein $R^1$ and $X^1$ have the same significance as described above; and $R^4$ represents an alkyl group having 1 to 4 carbon atom). According to this process, the desired triazine derivatives represented by general formula [I] can be efficiently obtained by reacting the trialkylamine salts represented by general formula [IV] with cyanoguanidine to prepare the alkyl biguanide salts represented by general formula [V], and then reacting the salts [V] with the alkyl esters represented by general formula [VI].

DETAILED DESCRIPTION OF THE PREFERRED EMBODIMENTS

Herein, in the reaction of the alkylamine salts represented by general formula [VI] with cyanoguanidine, both compounds may be used in eguimolar amounts. As a solvents, there may be used cyclic hydrocarbons such as benzene, decaline, alkylnaphthalenes, etc.; chlorinated hydrocarbons such as carbon tetrachroride, ethylene dichloride, chlorobenzene, dichlorobenzene, trichlorobenzene, etc. A reaction temperature is not particularly limited but the reaction sufficiently proceeds at a high temperature ranging from 80° to 200° C.

According to this reaction, the alkylbiguanide derivative salts shown by general formula [V] are obtained. By reacting [V] with alkyl esters represented by general formula [VI], the desired triazine derivatives represented by general formula [I] are prepared. This reaction efficiently proceeds generally in a solvent such as alcohols, e.g., methanol, ethanol, isopropanol, etc., various ketones, aliphatic hydrocarbons, various ethers, various cyclic hydrocarbons, chlorinated hydrocarbons, etc., in the presence of a catalyst such as a base, etc. at a temperature of about 10° to about 100° C.

Optical isomers are also present in these compounds and the products are obtained generally in the racemic form. However, it is also possible to the respective enantiomers in a conventional manner such as asymmetric synthesis, etc. In the present invention, both racemic compounds and optical isomers alone may be used. In the present invention, the products may be in the form of salts with inorganic acids or organic acid.

Turning to the phenoxy type herbicides represented by general formula [II] described above, specific examples include 2,4-dichlorophenoxyacetic acid, 2-methyl-4-chlorophenoxyacetic acid, 2-(2,4-dichlorophenoxy)-propionic acid, 2-(2-methyl-4-chlorophenoxy)propionic acid, 2-(2,4-dichlorophenoxy)butyric acid, 4-(2-methyl-4-chlorophenoxy) butyric acid, etc. Among them, 2-(2,4-dichlorophenoxy) propionic acid, 2-methyl-4-chlorophenoxyacetic acid, 2-(2-methyl-4-chlorophenoxy)propionic acid and 4-(2-methyl-4-chlorophenoxy)butyric acid are preferred.

The phenoxy type herbicides represented by general formula [II] described above may be prepared by known methods. These phenoxy type herbicides have an excellent herbicidal effect on broad-leaved weeds such as a toothcup (Rotala indica), a chickweed (Stellaria media), etc., but do not have sufficiently herbicidal effect on Graminae weeds or perennial weeds.

The first herbicidal composition of the present invention comprises as active ingredients the triazine derivatives represented by general formula [I] described above and the phenoxy type herbicides represented by general formula [II] described above. A proportion of these components to be formulated is not particularly limited but in a wide range of proportion, an excellent synergistic effect can be obtained. In general, it is preferred to formulate the triazine derivative and the phenoxy type herbicide in a range of from 10 : 1 to 1 : 50 (weight ratio).

Next, the second herbicidal composition of the present invention comprises as active ingredients the triazine derivatives represented by general formula [I] described above, the phenoxy type herbicides represented by general formula [II] described above and the urea type herbicides represented by general formula [III] described above.

Specific examples of the urea type herbicides represented by general formula [III] described above include N'-phenyl-N,N-dimethylurea, N'-(3-trifluoromethylphenyl)-N,N-dimethylurea, N'-(3,4-dichloropheyl)-N,N-dimethylurea, N'-(3-chloro- 4-methylphenyl)-N,N-dimethylurea, N'-(4-isopropylphenyl)-N,N-dimethylurea, N'-(4-chlorophenyl)-N-methoxy-N-methylurea, N'-(3,4-dichloropheyl)-N-methoxy-N-methylurea, N'-2-benzothiazoyl-N',N-dimethylurea, etc. Among them, preferred are N'-(3,4-dichloropheyl)-N,N-dimethylurea, N'-(3-chloro-4-methylphenyl)-N,N-dimethylurea, N'-(4-isopropylphenyl)-N,N-dimethylurea, N'-(3,4-dichloropheyl)-N-methoxy-N-methylurea and N'-2-benzothiazoyl-N',N-dimethylurea.

The urea type herbicides represented by general formula [III] described above may be prepared by known methods. The urea type herbicides have an excellent herbicidal effect on Gramineae weeds but do not have sufficiently herbicidal effect on some broad-leaved weeds such as Galium aparine L., Veronica hedelifolia, Viola arvensis, etc.

The second herbicidal composition of the present invention comprises as active ingredients the triazine derivatives represented by general formula [I] described above, the phenoxy type herbicides represented by general formula [II] described above and the urea type herbicides. A proportion of these components to be formulated is not particularly limited but in a wide range of proportion, an excellent synergistic effect can be obtained. In general, it is preferred to formulate the triazine derivative, the phenoxy type herbicide and the urea type herbicides in a range of from 10 : 1 : 1 to 1 : 50 : 100 (weight ratio).

The herbicidal composition of the present invention may be used in the form of wettable powders, emulsifiable concentrates, dusts, granules, flowable concentrates, solutions, etc., by blending the triazine derivatives represented by general formula [I] described above and the phenoxy type herbicides represented by general formula [II] described above, or blending the triazine derivatives represented by general formula [I] described above, the phenoxy type herbicides represented by general formula [II] described above and the urea type herbicides represented by general formula [III] described above, with liquid carriers such as solvents, etc. or with solid carriers such as mineral powders, etc. In preparing into these forms, there may be added surfactants such as emulsifiers, dispersing agents, developers, suspending agents, permeating agents, stabilizers, etc. and, if necessary, other auxiliary agents.

Where the herbicidal composition of the present invention is used in the form of wettable powders, 10 to 55 wt. % of the aforesaid triazine derivatives and the phenoxy type herbicide, or the triazine derivatives, the phenoxy type herbicide and the urea type herbicide as active ingredients, 40 to 88 wt. % of the solid carrier and 2 to 5 wt. % of the surfactant may generally be formulated to prepare a composition and the composition may be used. Where the herbicidal composition is used in the form of emulsifiable concentrate or flowable concentrate, 5 to 50 wt. % of the aforesaid triazine derivatives and the phenoxy type herbicide, or the triazine derivatives, the phenoxy type herbicide and the urea type herbicide as active ingredients, 35 to 90 wt. % of the solvent and 5 to 15 wt. % of the surfactant and other auxiliary agent may generally be formulated to prepare a composition and the resulting composition may be used.

Where herbicidal composition is used in the form of dust, 1 to 15 wt. % of the aforesaid triazine derivatives and the phenoxy type herbicide, or the triazine derivatives, the phenoxy type herbicide and the urea type herbicide as active ingredients and 85 to 99 wt. % of the solid carrier may generally be formulated to prepare a composition. Where herbicidal composition of the present invention is used in the form of granules, 0.1 to 15 wt. % of the aforesaid triazine derivatives and the phenoxy type herbicide, or the triazine derivatives, the phenoxy type herbicide and the urea type herbicide as active ingredients, 80 to 97.9 wt. % of the solid carrier and 2 to 5 wt. % of the surfactant may generally be formulated to prepare a composition. Herein, as the solid carrier, finely divided mineral powders are used. As the finely divided mineral powders, there are diatomaceous earth, oxides such as slaked lime, etc.; phosphates such as apatite, etc.; sulfates such as gypsum, etc.; silicates such as talc, pyrophyllite, clay, kaolin, bentonite, acid clay, white carbon, quartz powders, silica powders, etc.

As the liquid carrier, there may be organic solvents, for example, paraffin type or naphthene type hydrocarbons such as kerosene, mineral oil, spindle oil, etc.; aromatic hydrocarbons such as benzene, toluene, xylene, etc.; chlorinated hydrocarbons such as o-chlorotoluene, trichloromethane, trichloroethylene, etc.; alcohols such as cyclohexanol, amyl alcohol, ethylene glycol, etc.; alcohol ethers such as ethylene glycol monomethyl ether, ethylenen glycol monoethyl ether, etc.; ketones such as isophorone, cyclohexanone, cyclohexenyl-cyclohexanone, etc.; ethers such as butyl cellosolve, dimethyl ether, methyl ethyl ether, etc.; esters such as isopropyl acetate, benzyl acetate, methyl phthalate, etc.; amides such as dimethylformamide, etc.; nitriles such as acetonitrile, propionitrile, etc.; sulfoxides such as dimethylsulfoxide, etc.; or a mixture thereof; or water and the like.

As the surfactant, there may be used any of anion type (alkylbenzene sulfonate, alkyl sulfonates, laurinamide sulfonate, etc.), nonion type (polyoxyethylene octyl ether, polyethylene glycol laurate, sorbitan alkyl esters, etc.), cation type (dimethyllaurylbenzyl ammonium chloride, laurylamine, stearyltrimethyl ammonium chloride, etc.) and amphoteric type (amino acids, betaine, etc.).

For purposes of improving properties of the preparation and enhancing the herbicidal effect, the herbicidal composition of the present invention may also contain high molecular compounds such as sodium alginate, carboxymethyl cellulose, carboxyvinyl polymer, gum arabic, hydroxypropylmethyl cellulose, etc. and auxiliary agents in combination.

The herbicidal composition of the present invention exhibits an excellent effect on weeds in field crops such as corn, sorghum, wheat, barley, oat, etc., as high degree of selective herbicide without causing any phytotoxicities to crops by pre-or post-emergence treatment to the soil or the foliage of weeds. The herbicidal composition shows a high herbicidal effect not only against annual weeds but also against perennial weeds and is extremely useful as a high degree of selective, herbicide without causing any phytotoxicities for paddy rice plants or lawns.

The herbicidal composition of the present invention also exhibits an excellent effect of controlling weeds grown in orchards or non-cultivated fields (factory areas, railways, roadsides, waterways, fallow grounds), etc., by treatment to the soil or to the foliage of weeds.

The herbicidal composition of the present invention is applied in an amount of about 0.1 to 10,000 g, preferably 1 to 1,000 g, per 10 ares. Where the composition is sprayed over the foliage of plant, the composition is diluted to about 1 to about 100,000 ppm, preferably 10 to 10,000 ppm and the diluted preparation is applied to the foliage.

The herbioidal composition of the present invention may also be used in combination with other herbicides. Examples of the conventional herbicids which can be used herein include diphenyl ether compounds, triazine compounds, carbamate compounds, thiocarbamate compounds, acid anilide compounds, pyrazole compounds, phosphoric acid compounds, sulfonylurea compounds, imidazolinone compounds, dinitroaniline compounds, bromoxinyl, ioxinyl, oxadiazone, etc.

Furthermore, the herbicidal composition of the present invention may also be used as admixture with insecticides, sterilizers, plant growth regulators, fertilizers, etc., if necessary.

Next, the present invention is described with reference to examples.

Firstly, a method for making formulations is specifically described by referring to formulation examples. In the following formulation examples, "part" refers to % by weight. As the triazine derivative (Compound A), the phenoxy type herbicide (Compound B) and the urea type herbicide (Compound C) compounds shown in Tables 1, 2 and 3 were used, respectively.

TABLE 1

| Compound No. | Structural Formula | Name of Compound |
|---|---|---|
| A-1 | (benzofuran-2'-yl)-C(CH₃)=CH(CH₃)-NH-[triazine with 4-C(F)(CH₃)(CH₃) and 2-NH₂] | 2-amino-4-[1-(benzofuran-2'-yl)ethylamino]-6-(α-fluoro, α-methylethyl)-s-triazine |
| A-2 | (benzofuran-2'-yl)-C(CH₃)=CH(CH₃)-NH-[triazine with 4-CH(F)(CH₃) and 2-NH₂] | 2-amino-4-[1-(benzofuran-2'-yl)ethylamino]-6-(α-fluoroethyl)-s-triazine |
| A-3 | (benzothiophen-2'-yl)-C(CH₃)=CH(CH₃)-NH-[triazine with 4-C(F)(CH₃)(CH₃) and 2-NH₂] | 2-amino-4-[1-(benzothiophen-2'-yl)ethylamino]-6-(α-fluoro, α-methylethyl)-s-triazine |
| A-4 | 3-CH₃-C₆H₄-O-CH₂-CH(CH₃)-NH-[triazine with 4-C(F)(CH₃)(CH₃) and 2-NH₂] | 2-amino-4-[α-fluoro, α-methylethyl-6-(2-3',5'-dimethylphenoxy)-1-methylethylamino]-s-triazine |
| A-5 | 3-F-C₆H₄-O-CH₂-CH(CH₃)-NH-[triazine with 4-C(F)(CH₃)(CH₃) and 2-NH₂] | 2-amino-4-(α-fluoro, α-methylethyl)-6-[2-(3'-fluorophenoxy)-1-methylethylamino]-s-triazine |
| A-6 | 3,5-(CH₃)₂-C₆H₃-O-CH₂-CH(CH₃)-NH-[triazine with 4-C(Cl)(CH₃)(CH₃) and 2-NH₂] | 2-amino-4-(α-chloro, α-methylethyl)-6-[2-(3',5'-dimethylphenoxy)-1-methylethylamino]-s-triazine |
| A-7 | 3,5-(CH₃)₂-C₆H₃-O-CH₂-CH(CH₃)-NH-[triazine with 4-C(F)(CH₃)(CH₃) and 2-NH₂] | 2-amino-4-(α-fluoro, α-methylethyl)-6-[2-(3',5'-dimethylphenoxy)-1-methylethylamino]-s-triazine |

TABLE 2

| Compound No. | Structural Formula | Name of Compound |
|---|---|---|
| B-1 | Cl-C₆H₃(Cl)-OCH₂COOH | 2,4-dichloro-phenoxyacetic acid |
| B-2 | Cl-C₆H₃(CH₃)-OCH₂COOH | 2-methyl-4-chloro-phenoxyacetic acid |
| B-3 | Cl-C₆H₃(CH₃)-OCH(CH₃)COOH | 2-(2-methyl-4-chlorophenoxy) propionic acid |
| B-4 | Cl-C₆H₃(CH₃)-OCH₂CH₂CH₂COOH | 4-(2-methyl-4-chlorophenoxy) butyric acid |

TABLE 3

| Compound No. | Structural Formula | Name of Compound |
|---|---|---|
| C-1 | 3,4-Cl₂-C₆H₃-NHC(O)N(CH₃)₂ | N'-(3,4-dichlorophenyl)-N,N-dimethylurea |
| C-2 | 3-Cl-4-CH₃-C₆H₃-NHC(O)N(CH₃)₂ | N'-(3-chloro-4-methyl-phenyl)-N,N-dimethylurea |
| C-3 | 4-(CH₃)₂CH-C₆H₄-NHC(O)N(CH₃)₂ | N'-(4-isopropylphenyl)-N,N-dimethylurea |
| C-4 | 3,4-Cl₂-C₆H₃-NHC(O)N(CH₃)(OCH₃) | N'-(3,4-dichlorophenyl)-N-methoxy-N-methylurea |
| C-5 | 2-benzothiazoyl-N=C(CH₃)-N(CH₃)C(O)NHCH₃ | N'-(2-benzothiazoyl)-N',N-dimethylurea |

Formulation Example 1
Wettable powders

| Component | Amount |
|---|---|
| Compound A-1 | 5 parts |
| Compound B-1 | 15 parts |
| Diatomaceous earth | 62 parts |
| White carbon | 15 parts |
| Sodium alkylbenzenesulfonate | 2 parts |
| Sodium lignin sulfonate | 1 part |

The foregoing components are blended with each other, uniformly kneaded and ground into powders to give 100 parts of wettable powders.

Formulation Example 2
Emulsifiable concentrate

| Component | Amount |
|---|---|
| Compound A-2 | 10 parts |
| Compound B-2 | 30 parts |
| Xylene | 20 parts |
| Dimethylformamide | 20 parts |
| Solpol 2806B (manufactured by Toho Chemical Industry, surfactant) | 20 parts |

The foregoing components are uniformly dissolved and blended to give 100 parts of emulsifiable concentrate.

Formulation Example 3
Dust

| Component | Amount |
|---|---|
| Compound A-3 | 0.6 part |
| Compound B-3 | 1.4 parts |
| Diatomaceous earth | 20 parts |
| Talc | 78 parts |

The foregoing components are blended with each other, uniformly kneaded and ground to give 100 parts of dusts.

Formulation Example 4
Granule

| Component | Amount |
|---|---|
| Compound A-4 | 1 part |
| Compound B-4 | 3 parts |
| Bentonite | 30 parts |
| Talc | 63 parts |

-continued

| Formulation Example 4 Granule | |
|---|---|
| Sodium lignin sulfonate | 3 parts |

The foregoing components are thoroughly blended with each other, uniformly mixed and ground into powders. Water is added to the powders. After kneading them well, the blend is grained and dried to give 100 parts of granules.

| Formulation Example 5 Flowable concentrate | |
|---|---|
| Compound A-5 | 10 parts |
| Compound B-2 | 15 parts |
| Methyl cellulose | 0.3 part |
| Colloidal silica | 1.5 parts |
| Sodium lignin sulfonate | 1 part |
| Polyoxyethylene nonyl phenyl ether | 2 parts |
| Water | 70.2 parts |

The foregoing components are thoroughly mixed and dispersed. The resulting slurry mixture is subjected to wet grinding to give 100 parts of stable flowable concentrate.

FORMULATION EXAMPLE 6

Wettable Powders

By uniformly blending 97 parts of clay (trademark: JIKURAITO, manufactured by JIKURAITO KOGYO) as a Carrier, 1.5 parts of alkylaryl sulfonate (trademark: NEOPELEX, manufactured by Kao Atlas Co., Ltd.) as a surfactant, 1.5 parts of nonionic and anionic surfactant (trademark: Solpol 800A, manufactured by Toho Chemical Industry Co., Ltd.) and grinding into powders, a carrier for wettable powders was obtained.

By uniformly blending 90 parts of this carrier for wettable powders and 10 parts of the triazine derivative shown in Table 1 (Compounds A-1 through A-7) or 10 parts of the phenoxy type herbicide shown in Table 2 (Compounds B-1 to B-4) and grinding into powders, wettable powders were obtained.

Furthermore, the carrier for wettable powders containing the triazine derivative obtained above was blended with the carrier for wettable powders containing the phenoxy type herbicide in definite amounts (ratios as active ingredients), uniformly kneaded and ground into powders to give wettable powders.

FORMULATION EXAMPLE 7

By uniformly blending 90 parts of the carrier for wettable powders obtained in Formulation Example 6 and 10 parts of the triazine derivative shown in Table 1 (Compounds A-1 through A-7) or 10 parts of the phenoxy type herbicide shown in Table 2 (Compounds B-1 to B-4) and the urea type herbicide shown in Table 3 (Compounds C-1 to C-5) and grinding into powders, wettable powders were obtained.

Furthermore, the carrier for wettable powders containing the triazine derivative obtained above was blended with the carrier for wettable powders containing the phenoxy type herbicide and the carrier for wettable powders containing the urea type herbicide in definite amounts (ratios as active ingredients), uniformly kneaded and ground into powders to give wettable powders.

EXAMPLE 1

Test On Post-emergence Treatment

Wagner's pots of 1/2000 ares were filled with soil from upland fields and planted with weed seeds of *Abutilon theophrasti, Ipomoea purpurea, Galium aparine* L. and *Viola arvensis* and crop seeds of corn, sorghum, wheat, barley and oat. The seeds were then covered with soil and cultivated in a greenhouse. An agueous suspension of a definite amount of the herbicide obtained in Formulation Example 6 was uniformly sprayed onto the foliage of 1.5 to 2.5 leaf stage of these weeds and 3 leaf stage of the crops at a spray volume corresponding to 100 liters/10 ares. Then, cultivation was performed in the greenhouse. After 20 days, crop injury and the herbicidal effect on the weeds were evaluated according to the criterion described below. The results are shown in Table 4.

| (Criterion for assessment) Degree of herbicidal effect | Percent of weed control (herbicidal rate) |
|---|---|
| 0 | less than 5% (little effective) |
| 1 | 5–20% |
| 2 | 20–40% |
| 3 | 40–70% |
| 4 | 70–80% |
| 5 | more than 90% (almost all killed) |

The herbicidal rate described above was determined according to the following equation by measuring the raw weight of weed on the ground in the treated group and the raw weight of weed on the ground in the untreated group.

$$\text{Herbicidal rate (\%)} = \left(1 - \frac{\text{Weight of weed on the ground in the treated group}}{\text{Weight of weed on the ground in the untreated group}}\right) \times 100$$

Degree of crop injury

0 ... no injury to crops
1 ... little injury to crops
2 ... some injury to crops
3 ... injury to crops
4 ... serious injury to crops
5 ... almost all crops are withered to death

TABLE 4

| Active ingredient | Dosage (g/10a) | Herbicidal Effect | | | | Crop Injury | | | | |
|---|---|---|---|---|---|---|---|---|---|---|
| | | Abutilon theophrasti | Galium aparine L. | Ipomoea purpurea | Viola arvensis | Corn | Sorghum | Wheat | Barley | Oat |
| Triazine Derivative | | | | | | | | | | |
| A-1 | 10 | 3 | 2 | 4 | 3 | 0 | 0 | 0 | 0 | 0 |

TABLE 4-continued

| | | | | | | | | | | |
|---|---|---|---|---|---|---|---|---|---|---|
| | 5 | 1 | 1 | 2 | 2 | 0 | 0 | 0 | 0 | 0 |
| A-2 | 10 | 4 | 3 | 4 | 4 | 0 | 0 | 0 | 0 | 0 |
| | 5 | 2 | 1 | 3 | 3 | 0 | 0 | 0 | 0 | 0 |
| A-3 | 10 | 3 | 2 | 4 | 3 | 0 | 0 | 0 | 0 | 0 |
| | 5 | 2 | 1 | 2 | 2 | 0 | 0 | 0 | 0 | 0 |
| A-4 | 10 | 3 | 3 | 4 | 4 | 0 | 0 | 0 | 0 | 0 |
| | 5 | 2 | 1 | 3 | 2 | 0 | 0 | 0 | 0 | 0 |
| A-5 | 10 | 4 | 3 | 5 | 4 | 0 | 0 | 0 | 0 | 0 |
| | 5 | 3 | 2 | 4 | 3 | 0 | 0 | 0 | 0 | 0 |
| A-6 | 10 | 3 | 3 | 5 | 4 | 0 | 0 | 0 | 0 | 0 |
| | 5 | 2 | 1 | 3 | 2 | 0 | 0 | 0 | 0 | 0 |
| A-7 | 10 | 4 | 3 | 5 | 4 | 0 | 0 | 0 | 0 | 0 |
| | 5 | 3 | 2 | 4 | 3 | 0 | 0 | 0 | 0 | 0 |
| Phenoxy Type Herbicide | | | | | | | | | | |
| B-1 | 50 | 4 | 3 | 3 | 3 | 0 | 0 | 0 | 0 | 0 |
| | 25 | 3 | 2 | 2 | 2 | 0 | 0 | 0 | 0 | 0 |
| B-2 | 50 | 3 | 3 | 3 | 3 | 0 | 0 | 0 | 0 | 0 |
| | 25 | 2 | 1 | 2 | 2 | 0 | 0 | 0 | 0 | 0 |
| B-3 | 50 | 3 | 4 | 4 | 3 | 0 | 0 | 0 | 0 | 0 |
| | 25 | 2 | 3 | 3 | 1 | 0 | 0 | 0 | 0 | 0 |
| B-4 | 50 | 4 | 3 | 3 | 4 | 0 | 0 | 0 | 0 | 0 |
| | 25 | 2 | 1 | 1 | 2 | 0 | 0 | 0 | 0 | 0 |

| Triazine derivative | | Phenoxy type herbicide | | Herbicidal Effect | | | | Crop Injury | | | | |
|---|---|---|---|---|---|---|---|---|---|---|---|---|
| Kind | Dosage (g/10a) | Kind | Dosage (g/10a) | *Abutilon theophrasti* | *Galium aparine* L. | *Ipomoea purpurea* | *Viola arvensis* | Corn | Sorghum | Wheat | Barley | Oat |
| A-1 | 10 | B-1 | 50 | 5 | 5 | 5 | 5 | 0 | 0 | 0 | 0 | 0 |
| | 10 | | 25 | 5 | 5 | 5 | 5 | 0 | 0 | 0 | 0 | 0 |
| | 5 | | 50 | 5 | 5 | 5 | 5 | 0 | 0 | 0 | 0 | 0 |
| | 5 | | 25 | 5 | 5 | 5 | 5 | 0 | 0 | 0 | 0 | 0 |
| A-1 | 10 | B-3 | 50 | 5 | 5 | 5 | 5 | 0 | 0 | 0 | 0 | 0 |
| | 10 | | 25 | 5 | 5 | 5 | 5 | 0 | 0 | 0 | 0 | 0 |
| | 5 | | 50 | 5 | 5 | 5 | 5 | 0 | 0 | 0 | 0 | 0 |
| | 5 | | 25 | 5 | 5 | 5 | 5 | 0 | 0 | 0 | 0 | 0 |
| A-2 | 10 | B-1 | 50 | 5 | 5 | 5 | 5 | 0 | 0 | 0 | 0 | 0 |
| | 10 | | 25 | 5 | 5 | 5 | 5 | 0 | 0 | 0 | 0 | 0 |
| | 5 | | 50 | 5 | 5 | 5 | 5 | 0 | 0 | 0 | 0 | 0 |
| | 5 | | 25 | 5 | 5 | 5 | 5 | 0 | 0 | 0 | 0 | 0 |
| A-2 | 10 | B-2 | 50 | 5 | 5 | 5 | 5 | 0 | 0 | 0 | 0 | 0 |
| | 10 | | 25 | 5 | 5 | 5 | 5 | 0 | 0 | 0 | 0 | 0 |
| | 5 | | 50 | 5 | 5 | 5 | 5 | 0 | 0 | 0 | 0 | 0 |
| | 5 | | 25 | 5 | 5 | 5 | 5 | 0 | 0 | 0 | 0 | 0 |
| A-2 | 10 | B-3 | 50 | 5 | 5 | 5 | 5 | 0 | 0 | 0 | 0 | 0 |
| | 10 | | 25 | 5 | 5 | 5 | 5 | 0 | 0 | 0 | 0 | 0 |
| | 5 | | 50 | 5 | 5 | 5 | 5 | 0 | 0 | 0 | 0 | 0 |
| | 5 | | 25 | 5 | 5 | 5 | 5 | 0 | 0 | 0 | 0 | 0 |
| A-5 | 10 | B-1 | 50 | 5 | 5 | 5 | 5 | 0 | 0 | 0 | 0 | 0 |
| | 10 | | 25 | 5 | 5 | 5 | 5 | 0 | 0 | 0 | 0 | 0 |
| | 5 | | 50 | 5 | 5 | 5 | 5 | 0 | 0 | 0 | 0 | 0 |
| | 5 | | 25 | 5 | 5 | 5 | 5 | 0 | 0 | 0 | 0 | 0 |
| A-5 | 10 | B-2 | 50 | 5 | 5 | 5 | 5 | 0 | 0 | 0 | 0 | 0 |
| | 10 | | 25 | 5 | 5 | 5 | 5 | 0 | 0 | 0 | 0 | 0 |
| | 5 | | 50 | 5 | 5 | 5 | 5 | 0 | 0 | 0 | 0 | 0 |
| | 5 | | 25 | 5 | 5 | 5 | 5 | 0 | 0 | 0 | 0 | 0 |
| A-5 | 10 | B-3 | 50 | 5 | 5 | 5 | 5 | 0 | 0 | 0 | 0 | 0 |
| | 10 | | 25 | 5 | 5 | 5 | 5 | 0 | 0 | 0 | 0 | 0 |
| | 5 | | 50 | 5 | 5 | 5 | 5 | 0 | 0 | 0 | 0 | 0 |
| | 5 | | 25 | 5 | 5 | 5 | 5 | 0 | 0 | 0 | 0 | 0 |
| A-5 | 10 | B-4 | 50 | 5 | 5 | 5 | 5 | 0 | 0 | 0 | 0 | 0 |
| | 10 | | 25 | 5 | 5 | 5 | 5 | 0 | 0 | 0 | 0 | 0 |
| | 5 | | 50 | 5 | 5 | 5 | 5 | 0 | 0 | 0 | 0 | 0 |
| | 5 | | 25 | 5 | 5 | 5 | 5 | 0 | 0 | 0 | 0 | 0 |
| A-6 | 10 | B-1 | 50 | 5 | 5 | 5 | 5 | 0 | 0 | 0 | 0 | 0 |
| | 10 | | 25 | 5 | 5 | 5 | 5 | 0 | 0 | 0 | 0 | 0 |
| | 5 | | 50 | 5 | 5 | 5 | 5 | 0 | 0 | 0 | 0 | 0 |
| | 5 | | 25 | 5 | 5 | 5 | 5 | 0 | 0 | 0 | 0 | 0 |
| A-2 | 10 | B-4 | 50 | 5 | 5 | 5 | 5 | 0 | 0 | 0 | 0 | 0 |
| | 10 | | 25 | 5 | 5 | 5 | 5 | 0 | 0 | 0 | 0 | 0 |
| | 5 | | 50 | 5 | 5 | 5 | 5 | 0 | 0 | 0 | 0 | 0 |
| | 5 | | 25 | 5 | 5 | 5 | 5 | 0 | 0 | 0 | 0 | 0 |
| A-3 | 10 | B-1 | 50 | 5 | 5 | 5 | 5 | 0 | 0 | 0 | 0 | 0 |
| | 10 | | 25 | 5 | 5 | 5 | 5 | 0 | 0 | 0 | 0 | 0 |
| | 5 | | 50 | 5 | 5 | 5 | 5 | 0 | 0 | 0 | 0 | 0 |
| | 5 | | 25 | 5 | 5 | 5 | 5 | 0 | 0 | 0 | 0 | 0 |
| A-3 | 10 | B-3 | 50 | 5 | 5 | 5 | 5 | 0 | 0 | 0 | 0 | 0 |
| | 10 | | 25 | 5 | 5 | 5 | 5 | 0 | 0 | 0 | 0 | 0 |
| | 5 | | 50 | 5 | 5 | 5 | 5 | 0 | 0 | 0 | 0 | 0 |
| | 5 | | 25 | 5 | 5 | 5 | 5 | 0 | 0 | 0 | 0 | 0 |
| A-4 | 10 | B-1 | 50 | 5 | 5 | 5 | 5 | 0 | 0 | 0 | 0 | 0 |
| | 10 | | 25 | 5 | 5 | 5 | 5 | 0 | 0 | 0 | 0 | 0 |
| | 5 | | 50 | 5 | 5 | 5 | 5 | 0 | 0 | 0 | 0 | 0 |

TABLE 4-continued

| | | | | | | | | | | | | |
|---|---|---|---|---|---|---|---|---|---|---|---|---|
| | 5 | | 25 | 5 | 5 | 5 | 5 | 0 | 0 | 0 | 0 | 0 |
| A-4 | 10 | B-3 | 50 | 5 | 5 | 5 | 5 | 0 | 0 | 0 | 0 | 0 |
| | 10 | | 25 | 5 | 5 | 5 | 5 | 0 | 0 | 0 | 0 | 0 |
| | 5 | | 50 | 5 | 5 | 5 | 5 | 0 | 0 | 0 | 0 | 0 |
| | 5 | | 25 | 5 | 5 | 5 | 5 | 0 | 0 | 0 | 0 | 0 |
| A-6 | 10 | B-3 | 50 | 5 | 5 | 5 | 5 | 0 | 0 | 0 | 0 | 0 |
| | 10 | | 25 | 5 | 5 | 5 | 5 | 0 | 0 | 0 | 0 | 0 |
| | 5 | | 50 | 5 | 5 | 5 | 5 | 0 | 0 | 0 | 0 | 0 |
| | 5 | | 25 | 5 | 5 | 5 | 5 | 0 | 0 | 0 | 0 | 0 |
| A-7 | 10 | B-1 | 50 | 5 | 5 | 5 | 5 | 0 | 0 | 0 | 0 | 0 |
| | 10 | | 25 | 5 | 5 | 5 | 5 | 0 | 0 | 0 | 0 | 0 |
| | 5 | | 50 | 5 | 5 | 5 | 5 | 0 | 0 | 0 | 0 | 0 |
| | 5 | | 25 | 5 | 5 | 5 | 5 | 0 | 0 | 0 | 0 | 0 |
| A-7 | 10 | B-2 | 50 | 5 | 5 | 5 | 5 | 0 | 0 | 0 | 0 | 0 |
| | 10 | | 25 | 5 | 5 | 5 | 5 | 0 | 0 | 0 | 0 | 0 |
| | 5 | | 50 | 5 | 5 | 5 | 5 | 0 | 0 | 0 | 0 | 0 |
| | 5 | | 25 | 5 | 5 | 5 | 5 | 0 | 0 | 0 | 0 | 0 |
| A-7 | 10 | B-3 | 50 | 5 | 5 | 5 | 5 | 0 | 0 | 0 | 0 | 0 |
| | 10 | | 25 | 5 | 5 | 5 | 5 | 0 | 0 | 0 | 0 | 0 |
| | 5 | | 50 | 5 | 5 | 5 | 5 | 0 | 0 | 0 | 0 | 0 |
| | 5 | | 25 | 5 | 5 | 5 | 5 | 0 | 0 | 0 | 0 | 0 |
| A-7 | 10 | B-4 | 50 | 5 | 5 | 5 | 5 | 0 | 0 | 0 | 0 | 0 |
| | 10 | | 25 | 5 | 5 | 5 | 5 | 0 | 0 | 0 | 0 | 0 |
| | 5 | | 50 | 5 | 5 | 5 | 5 | 0 | 0 | 0 | 0 | 0 |
| | 5 | | 25 | 5 | 5 | 5 | 5 | 0 | 0 | 0 | 0 | 0 |

Some data were extracted from the results shown in Table 4 and the synergistic effect of the triazine derivative and the phenoxy type herbicide was examined on *Ipomoea purpurea* and *Viola arvensis* according to the following method.

$$Q_E = Q_a + Q_b - \frac{Q_a \cdot Q_b}{100}$$

$Q_a$: found data (%) of herbicidal rate when treated at a dosage corresponding to a g/10 ares using the triazine derivative alone as active ingredient $Q_b$: found data (%) of herbicidal rate when treated at a dosage corresponding to b g/10 ares using the phenoxy derivative alone as active ingredient $Q_E$: expected value [Limpel, L. E., P. H. Schuldt and D. Lamont, Proc. NEWCC, 16, 48-53 (1962)]

Herein, when the found data (herbicidal rate) of the herbicidal obtained by mixing the triazine derivative and the phenoxy type herbicide is larger than $Q_E$, it can be said that the herbicidal activity is synergistic. The results are shown in Table 5.

TABLE 5

| Triazine derivative | | Phenoxy type herbicide | | Herbicidal Effect | | | |
|---|---|---|---|---|---|---|---|
| Kind | Dosage (g/10a) | Kind | Dosage (g/10a) | Herbicidal Rate of *Ipomoea purpurea* (%) | Expected Value $(Q_E)$ (%) | Herbicidal Rate of *Viola arvensis* (%) | Expected Value $(Q_E)$ (%) |
| — | — | B-1 | 50 | 44 | — | 52 | — |
| — | — | B-2 | 50 | 58 | — | 48 | — |
| — | — | B-3 | 50 | 54 | — | 62 | — |
| — | — | B-4 | 50 | 72 | — | 74 | — |
| A-1 | 5 | — | — | 36 | — | 38 | — |
| A-1 | 5 | B-1 | 50 | 92 | 65 | 93 | 70 |
| A-1 | 5 | — | — | 36 | — | 38 | — |
| A-1 | 5 | B-3 | 50 | 93 | 70 | 93 | 76 |
| A-2 | 5 | — | — | 58 | — | 64 | — |
| A-2 | 5 | B-1 | 50 | 94 | 76 | 97 | 83 |
| A-2 | 5 | — | — | 58 | — | 64 | — |
| A-2 | 5 | B-2 | 50 | 96 | 82 | 92 | 81 |
| A-2 | 5 | — | — | 58 | — | 64 | — |
| A-2 | 5 | B-3 | 50 | 90 | 81 | 91 | 86 |
| A-2 | 5 | — | — | 58 | — | 64 | — |
| A-2 | 5 | B-4 | 50 | 93 | 88 | 94 | 90 |
| A-3 | 10 | — | — | 72 | — | 62 | — |
| A-3 | 10 | B-1 | 50 | 97 | 84 | 93 | 82 |
| A-3 | 10 | — | — | 72 | — | 62 | — |
| A-3 | 10 | B-3 | 50 | 96 | 87 | 95 | 86 |
| A-4 | 5 | — | — | 52 | — | 38 | — |
| A-4 | 5 | B-1 | 50 | 90 | 73 | 91 | 70 |
| A-4 | 5 | — | — | 52 | — | 38 | — |
| A-4 | 5 | B-3 | 50 | 91 | 78 | 92 | 76 |
| A-5 | 5 | — | — | 72 | — | 68 | — |
| A-5 | 5 | B-1 | 50 | 92 | 84 | 94 | 85 |
| A-5 | 5 | — | — | 72 | — | 68 | — |
| A-5 | 5 | B-2 | 50 | 95 | 88 | 92 | 83 |
| A-5 | 5 | — | — | 72 | — | 68 | — |
| A-5 | 5 | B-3 | 50 | 98 | 87 | 100 | 88 |
| A-5 | 5 | — | — | 72 | — | 68 | — |
| A-5 | 5 | B-4 | 50 | 100 | 92 | 96 | 92 |

TABLE 5-continued

| Triazine derivative | | Phenoxy type herbicide | | Herbicidal Effect | | | |
|---|---|---|---|---|---|---|---|
| | | | | Herbicidal Rate of *Ipomoea purpurea* (%) | Expected Value ($Q_E$) (%) | Herbicidal Rate of *Viola arvensis* (%) | Expected Value ($Q_E$) (%) |
| Kind | Dosage (g/10a) | Kind | Dosage (g/10a) | | | | |
| A-6 | 5 | — | — | 63 | — | 36 | — |
| A-6 | 5 | B-1 | 50 | 91 | 79 | 90 | 69 |
| A-6 | 5 | — | — | 63 | — | 36 | — |
| A-6 | 5 | B-3 | 50 | 93 | 83 | 93 | 76 |
| A-7 | 5 | — | — | 70 | — | 58 | — |
| A-7 | 5 | B-1 | 50 | 90 | 83 | 91 | 80 |
| A-7 | 5 | — | — | 70 | — | 58 | — |
| A-7 | 5 | B-2 | 50 | 94 | 87 | 92 | 78 |
| A-7 | 5 | — | — | 70 | — | 58 | — |
| A-7 | 5 | B-3 | 50 | 92 | 86 | 94 | 84 |
| A-7 | 5 | — | — | 70 | — | 58 | — |
| A-7 | 5 | B-4 | 50 | 99 | 92 | 96 | 89 |

EXAMPLE 2

Field Test (Pre-emergence Treatment Test)

Test zone having each plot of 2 m² were prepared and weed seeds of *Galium aparine* L., *Stellaria media*, *Viola arvensis*, *Matricaria inodora*, *Veronica hedelifolia*, *Papaver rhoeas* and *Aphanes arvensis* and crop seeds of wheat and barley were simultaneously planted.

At the pre-emergence timing of wheat, barley and weeds, a given amount of a dilution of the herbicide obtained in Formulation Example 6 was uniformly sprayed over the soil surface at a spray volume corresponding to 20 liters/10 ares.

The test was carried out by 3 replications.

The weeds on the ground which survived 60 days after spraying of the chemical were cut out and their raw weight were measured. According to the following equation, a weed controlling rate was determined as an average of the 3 replicates.

Percent of weed control (%) =

$$\left(1 - \frac{\text{Weight of survived weed on the ground in the treated plot}}{\text{Weight of survived weed on the ground in the untreated plot}}\right) \times 100$$

With respect to wheat and barley, their raw weights on the ground were measured also as in weeds and the degree of crop injury (inhibition rate) was determined. The results are shown in Table 6.

TABLE 6

| | Active ingredient | | | |
|---|---|---|---|---|
| | A-2 + B-3 | | A-7 + B-3 | |
| | Dosage (g/10a) | | | |
| | 20 + 120 | 10 + 120 | 20 + 120 | 10 + 120 |
| % of Weed Control | | | | |
| *Galium aparine* L. | 100 | 100 | 100 | 100 |
| *Stellaria media* | 100 | 100 | 100 | 100 |
| *Viola arvensis* | 100 | 100 | 100 | 100 |
| *Matricaria inodora* | 100 | 100 | 100 | 100 |
| *Veronica hedelifolia* | 100 | 100 | 100 | 100 |
| *Papaver rhoeas* | 100 | 100 | 100 | 100 |
| *Aphanes arvensis* | 100 | 100 | 100 | 100 |
| Crop Injury | | | | |
| Wheat | 0 | 0 | 0 | 0 |
| Barley | 0 | 0 | 0 | 0 |

EXAMPLE 3

Field Test (Post-emergence Treatment Test)

Test zones having each plot of 2 m² were prepared and weed seeds of *Galium aparine* L., *Stellaria media*, *Viola arvensis*, *Matricaria inodora*, *Veronica hedelifolia*, *Papaver rhoeas* and *Aphanes arvensis* and crop seeds of wheat and barley were simultaneously planted.

When weeds grew at the 2-3 leaf stage and wheat and barley reached the 3-leaf stage, a given amount of a dilution of the herbicide obtained in Formulation Example 6 was uniformly sprayed onto the foliage at a spray volume corresponding to 20 liters/10 ares.

The percent of weed control and the degree of crop injury were determined 30 days after spraying the chemical in a manner similar to Example 2. The results are shown in Table 7.

TABLE 7

| | Active ingredient | | | |
|---|---|---|---|---|
| | A-2 + B-3 | | A-7 + B-3 | |
| | Dosage (g/10a) | | | |
| | 20 + 60 | 10 + 60 | 20 + 60 | 10 + 60 |
| % of Weed Control | | | | |
| *Galium aparine* L. | 100 | 100 | 100 | 100 |
| *Stellaria media* | 100 | 100 | 100 | 100 |
| *Viola arvensis* | 100 | 100 | 100 | 100 |
| *Matricaria inodora* | 100 | 100 | 100 | 100 |
| *Veronica hedelifolia* | 100 | 100 | 100 | 100 |
| *Papaver rhoeas* | 100 | 100 | 100 | 100 |
| *Aphanes arvensis* | 100 | 100 | 100 | 100 |
| Crop Injury | | | | |
| Wheat | 0 | 0 | 0 | 0 |
| Barley | 0 | 0 | 0 | 0 |

EXAMPLE 4

Field Test (Post-emergence Treatment Test)

Test zones having each plot of 2 m² were prepared and weed seeds of *Xanthium strumarium*, *Ipomoea purpurea*, *Abutilon theophrasti*, *Portulaca oleracea*, *Solanum nigrum*, *Cassia obtusifolia* L., and *Amaranthus retroflexus* and crop seeds of corn and sorghum were simultaneously planted.

When weeds grew at the 2-3 leaf stage and corn and sorghum reached the 3-leaf stage, a given amount of a dilution of the herbicide obtained in Formulation Example 6 was uniformly sprayed onto the foliage at a spray volume corresponding to 20 liters/10 ares. The percent of weed control and the degree of crop injury were determined 30 days after spraying the chemical in a manner similar to Example 2. The results are shown in Table 8.

TABLE 8

| | Active ingredient | | |
|---|---|---|---|
| | A-7 + B-1 | | |
| | Dosage (g/10a) | | |
| | 20 + 20 | 10 + 20 | 5 + 20 |
| % of Weed Control | | | |
| Xanthium strumarium | 100 | 100 | 100 |
| Ipomoea purpurea | 100 | 100 | 100 |
| Abutilon theophrasti | 100 | 100 | 100 |
| Portulaca oleracea | 100 | 100 | 100 |
| Solanum nigrum | 100 | 100 | 100 |
| Cassia obtusifolia L. | 100 | 100 | 100 |
| Amaranthus retroflexus | 100 | 100 | 100 |
| Crop Injury | | | |
| Corn | 0 | 0 | 0 |
| Sorghum | 0 | 0 | 0 |

EXAMPLE 5

Field Test (Post-emergence Treatment Test)

Test zones having each plot of 2 m² were prepared and weed seeds of *Alopecurus myosuroides, Poa annua, Galium aparine* L., *Stellaria media, Viola arvensis, Matricaria inodora, Veronica hedelifolia, Papaver rhoeas* and *Apanes arvensis* and crop seeds of wheat and barley were simultaneously planted.

When weeds grew at the 2-3 leaf stage and wheat and barley reached the 3-leaf stage, a given amount of a dilution of the herbicide obtained in Formulation Example 6 was uniformly sprayed onto the foliage at a spray volume corresponding to 20 liters/10 ares.

The percent of weed control and the degree of crop injury were determined 30 days after spraying the chemical in a manner similar to Example 2. The results are shown in Table 9.

TABLE 9

| | Active ingredient | | | |
|---|---|---|---|---|
| | A-2 + B-3 + C-3 | | A-7 + B-3 + C-3 | |
| | Dosage (g/10a) | | | |
| | 20 + 60 + 200 | 10 + 60 + 200 | 20 + 60 + 200 | 10 + 60 + 200 |
| % of Weed Control | | | | |
| Alopecurus myosuroides | 100 | 100 | 100 | 100 |
| Poa annua | 100 | 100 | 100 | 100 |
| Galium aparine L. | 100 | 100 | 100 | 100 |
| Stellaria media | 100 | 100 | 100 | 100 |
| Viola arvensis | 100 | 100 | 100 | 100 |
| Matricaria inodora | 100 | 100 | 100 | 100 |
| Veronica hedelifolia | 100 | 100 | 100 | 100 |
| Papaver rhoeas | 100 | 100 | 100 | 100 |
| Aphanes arvensis | 100 | 100 | 100 | 100 |
| Crop Injury | | | | |
| Wheat | 0 | 0 | 0 | 0 |
| Barley | 0 | 0 | 0 | 0 |

By the synergistic effect of the triazine derivative and phenoxy type herbicide as active ingredient, the herbicidal composition of the present invention show a high herbicidal effect at a low dosage and also have a wide range of hebicidal spectrum. Further when the composition is used as herbicide for field crops, the composition has flexibility of treatment to exhibit effectiveness, as compared to in conventional herbicides for field crops. The composition also shows a high herbicidal activity even against troublesome weeds both by treatment to the soil at the pre- or post-emergence of weeds and by treatment to the foliage at the post-emergence of weeds. In addition, no crop injury is caused. In particular, the effect is markedly high in treatment to the soil or foliage treatment in fields where Gramineae crops grow. Further using by blending the mixture of the triazine derivative and the phenoxy type herbicide with the urea type herbicide, the composition exhibits a high hebicidal effect not only against broad-leaved weeds grown in Gramineae crops but also against Gramineae weeds. Accordingly, the herbicidal composition of the present invention has a very wide herbicidal spectrum as compared to conventional herbicides for field crops.

While the invention has been described in detail and with reference to specific embodiments thereof, it is apparent to one skilled in the art that various changes and modifications can be made therein without departing from the spirit and the scope of the present invention.

What is claimed is:

1. A herbicidal composition comprising as active ingredients a herbicidally effective amount of a triazine compound represented by general formula (I):

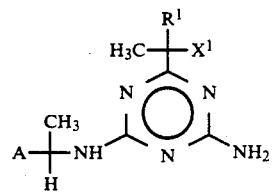

Wherein A represents the following formula (a):

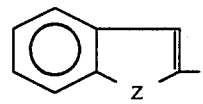

wherein Z represents oxygen atom or sulfur atom, or formula

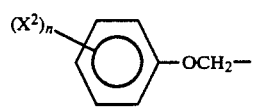

wherein X² represents methyl group or fluorine atom and n represents 0 or an integer of 1 or 2; R¹ represents hydrogen atom or methyl group; and X¹ represents fluorine atom or chlorine atom, and a herbicidally effective amount of a phenoxy type herbicide represented by general formula (II):

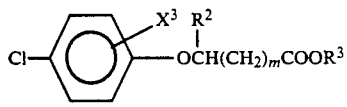 [II]

wherein $X^3$ represents methyl group or chlorine atom; $R^2$ represents hydrogen atom or methyl group; $R^3$ represents hydrogen atom, an alkyl group having 1 to 4 carbon atoms, an alkenyl group having 1 and 4 carbon atoms, sodium atom or $NH_4$; and m represents 0 or an integer of 1 to 3.

2. A herbicidal composition comprising as active ingredients a herbicidally effective amount of a triazine compound represented by general formula (I):

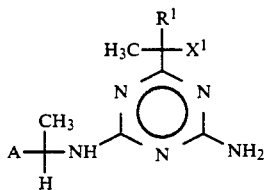 [I]

wherein A represents the following formula (a):

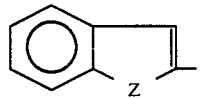 (a)

wherein Z represents oxygen atom or sulfur atom, or formula (b):

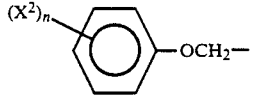 (b)

wherein $X^2$ represents methyl group or fluorine atom and n represents 0 or an integer of 1 or 2; $R^1$ represents hydrogen atom or methyl group; and $X^1$ represents fluorine atom or chlorine atom, a herbicidally effective amount of a phenoxy type herbicide represented by general formula (II):

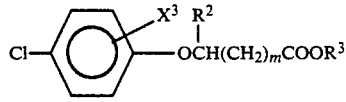 [II]

wherein $X^3$ represents methyl group or chlorine atom; $R^2$ represents hydrogen atom or methyl group; $R^3$ represents hydrogen atom, an alkyl group having 1 to 4 carbon atoms, an alkenyl group having 1 to 4 carbon atoms, sodium atom or $NH_4$; and m represents 0 or an integer of 1 to 3, and a herbicidally effective amount of a urea type herbicide represented by general formula (III):

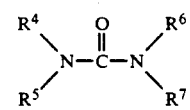 [III]

wherein $R^4$ represents a benzene ring or an aromatic hetero ring, which may be optionally substituted; $R^5$ represents hydrogen atom or a straight or branched alkyl group having 1 to 6 carbon atoms; $R^6$ represents a straight or branched alkyl group having 1 to 6 carbon atoms; $R^7$ represents hydrogen atom or a straight or branched alkyl group or a branched alkoxy group, having 1 to 6 carbon atoms.

3. The herbicidal composition as claimed in claim 1, wherein the triazine compound is selected from the group consisting of
2-amino-4-[1-(benzofuran-2'-yl)ethylamino]-6-(α-fluoro, α-methylethyl)-s-triazine,
2-amino-4-[1-(benzofuran-2'-yl)ethylamino]-6(α-fluoroethyl)-s-triazine,
2-amino-4-[1-(benzothiophen-2'-yl)ethylamino]-6-(α-fluoro,α-methylethyl)-s-triazine,
2-amino-4-[α-fluoro,α-methylethyl-6-(2-3',5'-dimethylphenoxy)-1-methylethylamino]-s-triazine,
2-amino-4-(α-fluoro,α-methylethyl)-6-[2-(3'-fluorophenoxy)-1-methyl-ethylamino]-s-triazine,
2-amino-4-(α-chloro,α-methylethyl)-6-[2-(3',5'-dimethylphenoxy)-1-methylethylamino]-s-triazine and
2-amino-4-(α-fluoro,α-methylethyl)-6-[2-(3',5'-dimethylphenoxy)-1-methylethylamino]-s-triazine.

4. The herbicidal composition as claimed in claim 3, wherein the phenoxy type herbicide is selected from the group consisting of
2,4-dichlorophenoxyacetic acid,
2-methyl-4-chlorophenoxyacetic acid,
2-(2-methyl-4-chlorophenoxy)propionic acid and
4-(2-methyl-4-chlorophenoxy)butyric acid.

5. The herbicidal composition as claimed in claim 4, wherein the triazine compound to the phenoxy type herbicide is in a weight ratio of 10:1 to 1:50.

6. The herbicidal composition as claimed in claim 5, wherein the triazine compound is 2-amino-4-(α-fluoro, α-methylethyl)-6-(2-(3',5'-dimethylphenoxy)-1-methylethylamino)-s-triazine and the phenoxy type herbicide is 2,4-dichlorophenoxyacetic acid.

7. A method of combatting weeds comprising applying to weeds or to a locus thereof an effective herbicidal amount of the composition according to claim 1.

8. The method as claimed in claim 7, wherein the triazine compound is selected from the group consisting of
2-amino-4-[1-(benzofuran-2'-yl)ethylamino]-6-(α-fluoro, α-methylethyl)-s-triazine,
2-amino-4-[1-(benzofuran-2'-yl)ethylamino]-6(α-fluoroethyl)-s-triazine,
2-amino-4-[1-(benzothiophen-2'-yl)ethylamino]-6-(α-fluoro,α-methylethyl)-s-triazine,
2-amino-4-[α-fluoro,α-methylethyl-6-(2-3',5'-dimethylphenoxy)-1-methylethylamino]-s-triazine,
2-amino-4-(α-fluoro,α-methylethyl)-6-[2-(3'-fluorophenoxy)-1-methylethylamino]-s-triazine,
2-amino-4-(α-chloro,α-methylethyl)-6-[2-(3',5'-dimethylphenoxy)-1-methylethylamino]-s-triazine and
2-amino-4-(α-fluoro,α-methylethyl)-6-[2-(3',5'-dimethylphenoxy)-1-methylethylamino]-s-triazine;

the phenoxy type herbicide is selected from the group consisting of 2,4-dichlorophenoxyacetic acid,
2-methyl-4-chlorophenoxyacetic acid,
2-(2-methyl-4-chlorophenoxy)propionic acid and
4-(2-methyl-4-chlorophenoxy)butyric acid;

and the triazine compound to the phenoxy type herbicide is in a weight ratio of 10:1 to 1:50.

9. The herbicidal composition as claimed in claim 2, wherein the triazine compound is selected from the group consisting of 2-amino-4-[1-(benzofuran-2'-yl)ethylamino]-6-(α-fluoro, α-methylethyl)-s-triazine,
2-amino-4-[1-(benzofuran-2'-yl)ethylamino]-6(α-fluoroethyl)-s-triazine,
2-amino-4-[1-(benzothiophen-2'-yl)ethylamino]-6-(α-fluoro,α-methylethyl)-s-triazine,
2-amino-4-[α-fluoro,α-methylethyl-6-(2-3',5'-dimethylphenoxy)-1-methylethylamino]-s-triazine,
2-amino-4-(α-fluoro,α-methylethyl)-6-[2-(3'-fluorophenoxy)-1-methylethylamino]-s-triazine,
2-amino-4-(α-chloro,α-methylethyl)-6-[2-(3',5'-dimethylphenoxy)-1-methylethylamino]-s-triazine and
2-amino-4-(α-fluoro,α-methylethyl)-6-[2-(3',5'-dimethylphenoxy)-1-methylethylamino]-s-triazine.

10. The herbicidal composition as claimed in claim 9, wherein the phenoxy type herbicide is selected from the group consisting of 2,4-dichlorophenoxyacetic acid,
2-methyl-4-chlorophenoxyacetic acid,
2-(2-methyl-4-chlorophenoxy)propionic acid and
4-(2-methyl-4-chlorophenoxy)butyric acid.

11. The herbicidal composition according to claim 10, wherein the urea type herbicide is selected from the group consisting of N'-(3,4-dichlorophenyl)-N,N-dimethylurea,
N'-(3-chloro-4-methylphenyl)-N,N-dimethylurea,
N'-(4-isopropylphenyl)-N,N-dimethylurea,
N'-(3,4-dichlorophenyl)-N-methoxy-N-methylurea and
N'-(2-benzothiazoyl)-N',N-dimethylurea.

12. The herbicidal composition as claimed in claim 11, wherein the triazine compound to the phenoxy type herbicide to the urea type herbicide is in a weight ratio of 10:1:1 to 1:50:100.

13. A method of combatting weeds comprising applying to weeds or to a locus thereof an effective herbicidal amount of the composition of claim 2.

14. The method as claimed in claim 13, wherein the triazine compound is selected from the group consisting of 2-amino-4-[1-(benzofuran-2'-yl)ethylamino]-6-(α-fluoro, α-methylethyl)-s-triazine,
2-amino-4-[1-(benzofuran-2'-yl)ethylamino]-6(α-fluoroethyl)-s-triazine,
2-amino-4-[1-(benzothiophen-2'-yl)ethylamino]-6-(α-fluoro,α-methylethyl)-s-triazine,
2-amino-4-[α-fluoro,α-methylethyl-6-(2-3',5'-dimethylphenoxy)-1-methylethylamino]-s-triazine,
2-amino-4-(α-fluoro,α-methylethyl)-6-[2-(3'-fluorophenoxy)-1-methylethylamino]-s-triazine,
2-amino-4-(α-chloro,α-methylethyl)-6-[2-(3',5'-dimethylphenoxy)-1-methylethylamino]-s-triazine and
2-amino-4-(α-fluoro,α-methylethyl)-6-[2-(3',5'-dimethylphenoxy)-1-methylethylamino]-s-triazine;

the phenoxy-type herbicide is selected from the group consisting of 2,4-dichlorophenoxyacetic acid,
2-methyl-4-chlorophenoxyacetic acid,
2-(2-methyl-4-chlorophenoxy)propionic acid and
4-(2-methyl-4-chlorophenoxy)butyric acid;

the urea type herbicide is selected from the group consisting of

N'-(3,4-dichlorophenyl)-N,N-dimethylurea,
N'-(3-chloro-4-methylphenyl)-N,N-dimethylurea,
N'-(4-isopropylphenyl)-N,N-dimethylurea,
N'-(3,4-dichlorophenyl)-N-methoxy-N-methylurea and
N'-(2-benzothiazoyl)-N',N-dimethylurea; and wherein the triazine compound to the phenoxy type herbicide to the urea type herbicide is in a weight ratio of 10:1:1:1 to 1:50:100.

* * * * *